US006570177B1

(12) United States Patent
Struckhoff et al.

(10) Patent No.: US 6,570,177 B1
(45) Date of Patent: May 27, 2003

(54) SYSTEM, APPARATUS, AND METHOD FOR DETECTING DEFECTS IN PARTICLES

(75) Inventors: Andy Struckhoff, Alexandria, VA (US); Yeu-Hwa Shyy, Fairfax, VA (US)

(73) Assignee: DCS Corporation, Alexandria, VA (US)

( * ) Notice: Subject to any disclaimer, the term of this patent is extended or adjusted under 35 U.S.C. 154(b) by 0 days.

(21) Appl. No.: 09/494,305

(22) Filed: Jan. 31, 2000

(51) Int. Cl.[7] .............................................. G01N 15/06
(52) U.S. Cl. ..................... 250/574; 250/222.1; 356/236
(58) Field of Search ............................... 250/574, 222.2, 250/228, 343; 356/246, 236, 436, 437; 348/126

(56) References Cited

U.S. PATENT DOCUMENTS

| 4,802,762 | A |   | 2/1989 | Hill, Jr. |
| 4,910,403 | A |   | 3/1990 | Kilham et al. |
| 5,187,765 | A |   | 2/1993 | Muehlemann et al. |
| 5,198,369 | A | * | 3/1993 | Iton et al. ................... 436/534 |
| 5,239,358 | A | * | 8/1993 | Tokoyama ................... 356/244 |
| 5,255,089 | A | * | 10/1993 | Dybas et al. ................ 358/101 |
| 5,256,886 | A |   | 10/1993 | Wolf et al. |
| 5,383,776 | A |   | 1/1995 | Trail et al. |
| 5,495,105 | A | * | 2/1996 | Nishimura et al. ......... 250/251 |
| 5,537,203 | A |   | 7/1996 | Carr |
| 5,786,894 | A | * | 7/1998 | Shields et al. .............. 356/338 |

* cited by examiner

Primary Examiner—Stephone B. Allen
(74) Attorney, Agent, or Firm—Shaw Pittman LLP

(57) ABSTRACT

A method and apparatus for automatically inspecting transparent or translucent materials, especially plastic materials, the apparatus including a light container, at least one camera, a digital processor, and a reject mechanism, the method comprising conveying a particle of the material through the light container, capturing an image of the particle with the camera, identifying defects in the image with the digital processor, and separating out defective material by communication between the digital processor and the reject mechanism. The light container is an illumination device, preferably an integrating sphere, that has two opposing openings through which a particle can pass and one or more other openings or windows through which one or more cameras view the particle.

27 Claims, 10 Drawing Sheets

SYSTEM, APPARATUS, AND METHOD FOR DETECTING DEFECTS IN PARTICLES

BACKGROUND

1. Field of the Invention

The present invention relates to a method and apparatus for material inspection, and more particularly, to a method and apparatus for detecting defects in transparent or translucent material particles and for separating a batch of material particles into portions of like grade or quality.

2. Background of the Invention

Material inspection is an essential part of any manufacturing process. Manufacturers must ensure that the raw materials used in manufacture meet or exceed standards of quality, such as size, color, and purity. Inferior raw materials degrade the quality of the final product and reduce the manufacturer's sales and profits. Thus, to maintain strict product specifications and satisfied customers, manufacturers demand that raw materials adhere to a minimum quality or grade.

Sensitive to such concerns, suppliers of raw materials routinely conduct inspections with objectives such as identifying and removing flawed material, assessing the overall quality of a batch of material, and separating a batch of material into portions of like size, color, purity, or grade. In the plastics industry, for example, suppliers inspect raw polymer pellets to identify manufacturing defects and to grade a certain lot of pellets for purity. Based on the grading information, suppliers can price lots according to their quality and can offer to manufacturers grades of pellets that meet minimum manufacturing requirements. In this manner, manufacturers do not have to pay for unnecessary purity and, in turn, can maintain competitive product pricing.

When inspecting material, suppliers and manufacturers look for a variety of defects, depending upon the type of material. In food products, for example, defects include foreign matter, uncooked portions, unprocessed or clumped portions, and contaminants from pests such as insects or rodents. In plastic pellets, defects generally include foreign matter, charred raw material, contaminants from unmelted base constituents of the polymer material (often referred to as gels), incorrectly sized or colored pellets, broken pellets, and pellets that are stuck to each other. In addition, manufacturers sometimes measure the amount of fines (small chips or thread-like pieces that can break away from the pellets during manufacturing and transportation).

Traditionally, material inspection has been a slow, labor-intensive process limited to testing small samples instead of all material that is incorporated into the final product. Thus, theoretically, a sample might not be representative of the defects present in the rest of the material. Although the following discussion of the traditional methods of inspection is in the context of the plastics industry, the methods and their associated drawbacks apply equally to other material inspections, e.g., food processing. In the plastics industry, the current methods for inspecting raw plastic material include: 1) visual inspection of pellets by a person; 2) inspection of polymer ribbons formed from pellets; 3) inspection of molten polymer; and 4) automated inspection of the pellets. It is important to note that these methods are typically suitable for base or raw materials that are transparent or translucent. Generally, however, this requirement is not a problem because coloring is usually added late in the manufacturing process.

Visual inspection of pellet material by a person is the most common method of material inspection. It is generally conducted in a quality control laboratory separate from the manufacturing process. The visual inspection method typically involves spreading a sample of particles on top of a light table (e.g., a glass or Plexiglas™ table with a light source below its top) or other white or light-colored surface, and examining each particle for a defect. If the size of a possible defect is small, the inspectors must strain their eyes to observe the defect or perhaps use a magnifying glass to focus on each particle. Although using the light table or light-colored surface enhances the defects, the process is only as reliable as the eyes and concentration of the human inspector. In addition to human error, using human inspectors increases labor costs and significantly reduces speed at which material is analyzed.

Inspection of polymer ribbons involves melting raw material pellets into a molten form, extruding the molten material into thin, ribbon-like shapes, and inspecting the ribbons for defects. The ribbon shapes are flatter than pellets, which eases handling and presents a larger viewable surface area. This ribbon inspection technique can be incorporated into manual (visual inspection by a person) and automated methods of inspection. Despite the advantages in handling and viewable surface area, the ribbon inspection technique suffers from the added time and expense of melting the raw material pellets. The equipment and manpower needed to accomplish this extra step add significantly to the overall cost of material inspection.

In addition to analyzing ribbons, some inspection techniques analyze the molten polymer itself, in a device known as a flow cell. The flow cell is a chamber with a conduit viewable through a window. U.S. Pat. No. 4,910,403 to Kilham and LeBlon discloses a flow cell typically used for the molten polymer inspection technique. The molten polymer is channeled through the conduit, illuminated, and inspected as it passes under the window. This inspection technique can analyze the molten material either manually or with an automated device. Although this method can identify defective portions of the molten polymer, the method cannot separate those defective portions from the remaining acceptable portions. Thus, the method is suitable for grading the molten polymer or monitoring a manufacturing process for quality control, but not for removing defective portions and improving the quality of the molten polymer. In addition, the flow cell and the equipment necessary to convey the molten polymer introduce additional costs and complexities to the inspection process.

Generally, automated inspection of polymer pellets involves passing the material in front of a device that detects defects using technologies such as photography, x-rays, and digital line scanners. For the plastics industry, the typical automated inspection method, which does not include the burdensome step of melting, takes a picture of a pellet as it passes in front of an illuminated background. FIG. 1 shows an example setup of this technique. A camera 100 takes a picture of a pellet 102 as it passes in front of a light source 104. Typically, light source 104 is an illumination source such as the fiber optic backlight disclosed in U.S. Pat. No. 5,187,765. A beam of light 106 illuminates the center of pellet 102 and reaches camera 100. For purposes of explanation and comparison, this application will refer to this automated inspection as the backlighting method.

Although the backlighting method can speed the inspection process, persons skilled in the art recognize that the method is not as accurate as the visual inspection method described above. Principally, the reduction in accuracy is due to the lighting of the round or almost round pellet. Because of the round surface, a clear polymer pellet exhibits a lensing effect that refracts light around the edges of the pellet, in much the same way that images are distorted around the perimeter of a crystal ball or marble. FIG. 2 shows how the light 200 is refracted or redirected as it passes through pellet 102. The pellet refracts light 200 so that the pellet edges appear to be illuminated only by the dull light around light source 104 instead of by the bright light originating from light source 104. As a result of the light refraction, pellet 102 appears darker at its edges than at its center. FIG. 3 illustrates an example of this lensing effect and the shadows that result along the edge of the pellet image. As evident in FIG. 3, if a defect exists at the edge of the pellet, the dark edges caused by the refraction hide the flaw and the automated detection device misses the defect. This error in inspection can lead to the costly consequences of an improperly graded material and an inferior final product.

Thus, there remains a need for an inspection method that incorporates automated inspection for speed and efficiency, yet does not miss defects due to the effect of light refraction by the pellet. The method should avoid the extra cost and time associated with melting the base material and should quickly assess the material and separate out defective portions. Further, the inspection method should maintain the accuracy standards required by material suppliers and product manufacturers.

SUMMARY OF THE INVENTION

The present invention is a method and apparatus for automatically inspecting materials. Although described in the context of plastic manufacturing, the present invention could be used in any process that inspects a transparent or translucent particle for defects, such as with food products or glass products. The present invention could also be used to inspect other types of particles, such as white particles, light colored particles, or opaque particles. If such particles are not transparent or translucent, the present invention will detect defects near or at the surface of the particles.

The primary components of the present invention include a light container, at least one camera, a digital processor, and a reject mechanism. Briefly stated, the present invention passes a particle through the light container, captures an image of the particle with the camera, identifies defects in the image with the digital processor, and separates out defective material by communication between the digital processor and the reject mechanism.

The light container is an illumination device that has two opposing openings through which a particle can pass and one or more other openings or windows through which one or more cameras view the particle. Preferably, the light container is an integrating sphere that collects light from an integral input light beam and acts a source of illumination. A commercial example of the light container is disclosed in U.S. Pat. No. 5,537,203, which describes an integrating sphere, constructed of a highly reflective diffuse material, either in the form of a surface coating or as a solid material. U.S. Pat. No. 5,537,203, is incorporated by reference herein. Upon entering the sphere, light from the input beam undergoes multiple reflections, scatters uniformly around the interior of the sphere, and produces spatially integrated light. Preferably, to avoid glares, the input beam transmits light into the light container in a direction away from the location at which the particle passes in front of the camera.

As a particle is dropped or otherwise conveyed through the light container, at least one camera captures an image of the fully illuminated particle. The light container ensures that all sides of the particle are illuminated such that even when viewing the edge of the particle, a line of refracted light still originates from the illuminated wall of the light container. In other words, because the particle is inside the light container, it is backlighted in all directions. The net result is an image of the particle without the dark edges that plague the methods of the prior art. FIG. 4a illustrates an image captured by the present invention with defects noted at points 400 and 402.

In a preferred embodiment of the present invention, the camera is a line scan camera that scans consecutive one-dimensional lines of the particle as the particle travels through the viewing field of the camera. Each one-dimensional line is stored in the memory buffer of the digital processor and assembled into a two-dimensional array. FIG. 4b is a schematic representation of the recording of one dimensional lines, 41 through 48, and the assembling of lines 41 through 48 into a two dimensional image 49. The two-dimensional array captures the image of the particle, like the image shown in FIG. 4a. Although the camera could be of any type, including traditional video cameras, line scan cameras are preferable because of their speed of operation.

In another preferred embodiment of the present invention, multiple cameras view the particle through the light container from varying angles. Multiple cameras reduce the possibility of missing a defect located on the back side of a particle. Such a possibility would be very rare for transparent particles, but could be more common with translucent or opaque particles, e.g., white or gray plastic, which greatly limit the passage of light. The cameras should be spaced equally around the integrating sphere in such a manner that no cameras are opposite each other (in which case a camera would capture the opposite camera in the image, producing a spot that looks like a defect).

The digital processor is a computer that stores data from the line scans of the camera, assembles the line scan data into two dimensional arrays, and looks for dark portions indicative of a defect. If the digital processor finds a defect in a particle, the digital processor directs the reject mechanism to activate at the precise moment the defective particle reaches the reject mechanism. The digital processor can be an individual component of the present invention or can be integrated with the camera as a single component. In this specification and in the claims, the term "computer" means a portion of a computer with software, a single computer with software, or one or more computers with software in communication with each other.

The reject mechanism is any device that, in response to a signal, separates a defective particle from the stream of particles entering and exiting the light container. Preferably, the reject mechanism is a pneumatic injector that redirects the path of a rejected falling particle with a short blast of air. Also, preferably, the redirected particles fall through a conduit separate from the non-defective particles, thereby creating separate piles or bins of defective and non-defective material.

In a preferred embodiment of the present invention, the above-described components work in concert in an automatic mode so that particles are delivered to the sphere, analyzed for defects, and separated into matching portions without human participation. Optionally, the automatic inspection is an in-line process completed during manufacturing so that all material used in a product is analyzed, not just a sample batch. In this embodiment, the processing speed of the line scan camera and the digital processor would equal or exceed the manufacturing speed of the assembly or manufacturing line.

The present invention is capable of detecting defects that the prior art backlighting devices have not been able to detect. Defects such as charred material and foreign matter appear as dark sections of the particle image, without being obscured by shadowed edges. In addition, as would be apparent to one skilled in the art, a preferred embodiment of the present invention would detect gels within a pellet, by changing the type of light, e.g., using an ultraviolet input light beam to cause the gel defect to fluoresce, and detecting the fluoresence in the visible spectrum by adding filters to the line scan camera.

Accordingly, an object of the present invention is to provide a method and apparatus for inspecting transparent, translucent, or opaque material.

Another object of the present invention is to provide an in-line material inspection process that analyzes all material used in a manufacturing process and identifies and removes all defective portions.

Another object of the present invention is to provide a method and apparatus that sufficiently illuminates a particle to accentuate defects and to eliminate shading that hides defects.

Another object of the present invention is to provide a method and apparatus that eliminates the possibility of missing a particle defect located on a side of the particle opposite to a camera.

These and other objects of the present invention are described in greater detail in the detailed description of the invention, the appended drawings, and the attached claims.

DETAILED DESCRIPTION OF THE INVENTION

Components of the Present Invention

Figure 1:
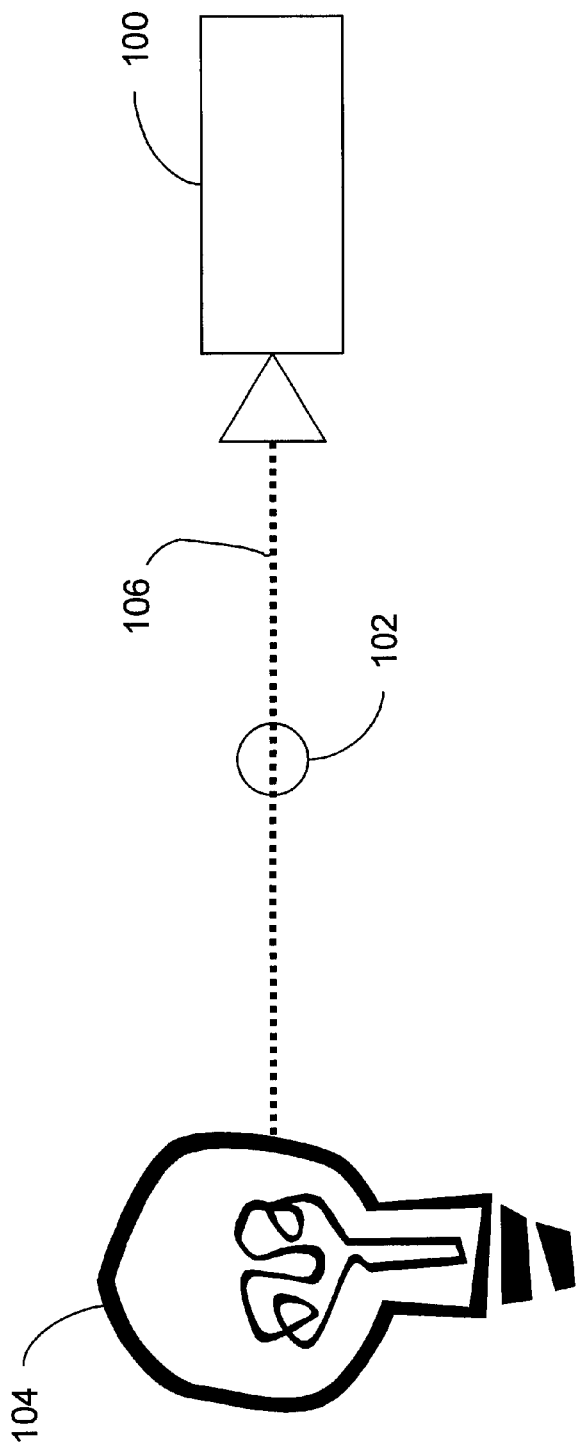
FIG. 1 is a schematic diagram of the backlighting method of material inspection used in the prior art.
Figure 2:
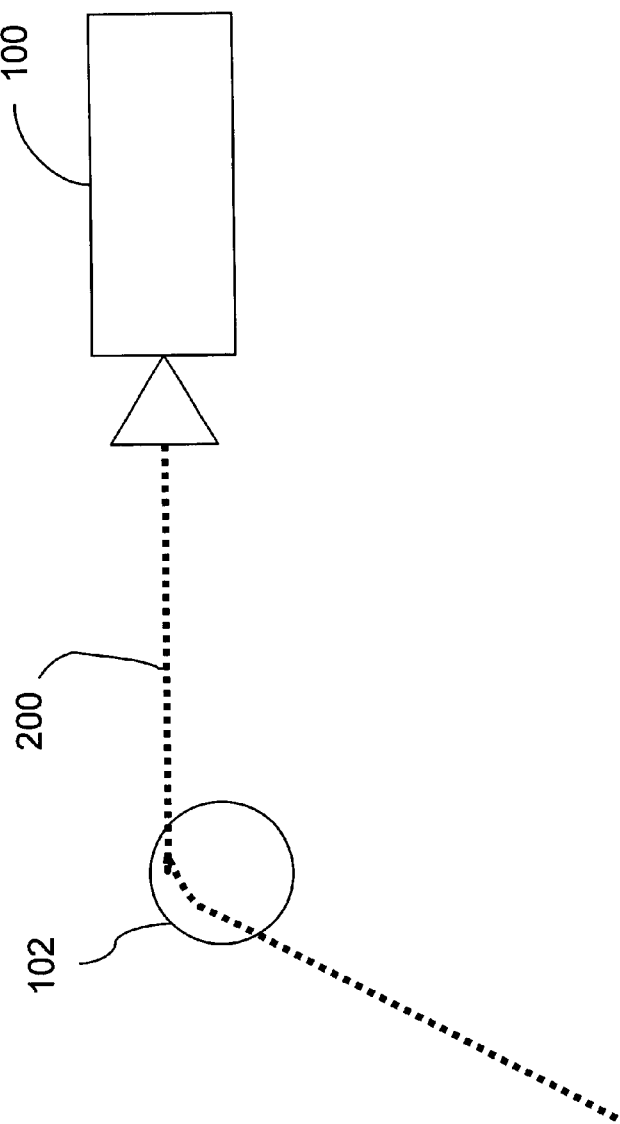
FIG. 2 is a schematic diagram showing the lensing effect, or refracted light, that occurs when the prior art backlighting method views light through the round edges of a pellet.
Figure 2:
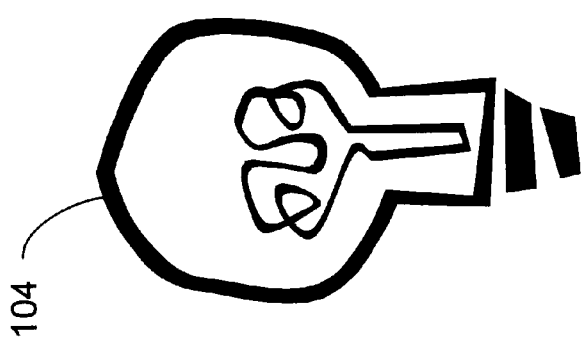
Figure 3:
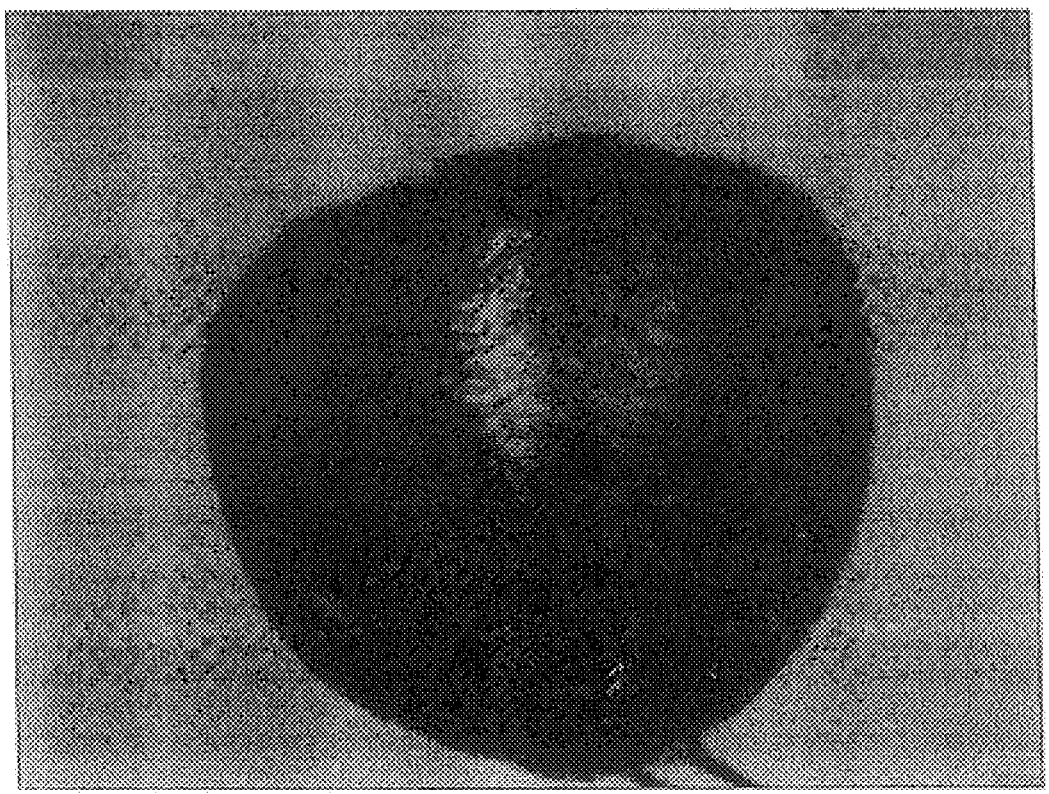
FIG. 3 is an image of a material particle created using the backlighting method of the prior art.
Figure 4A:
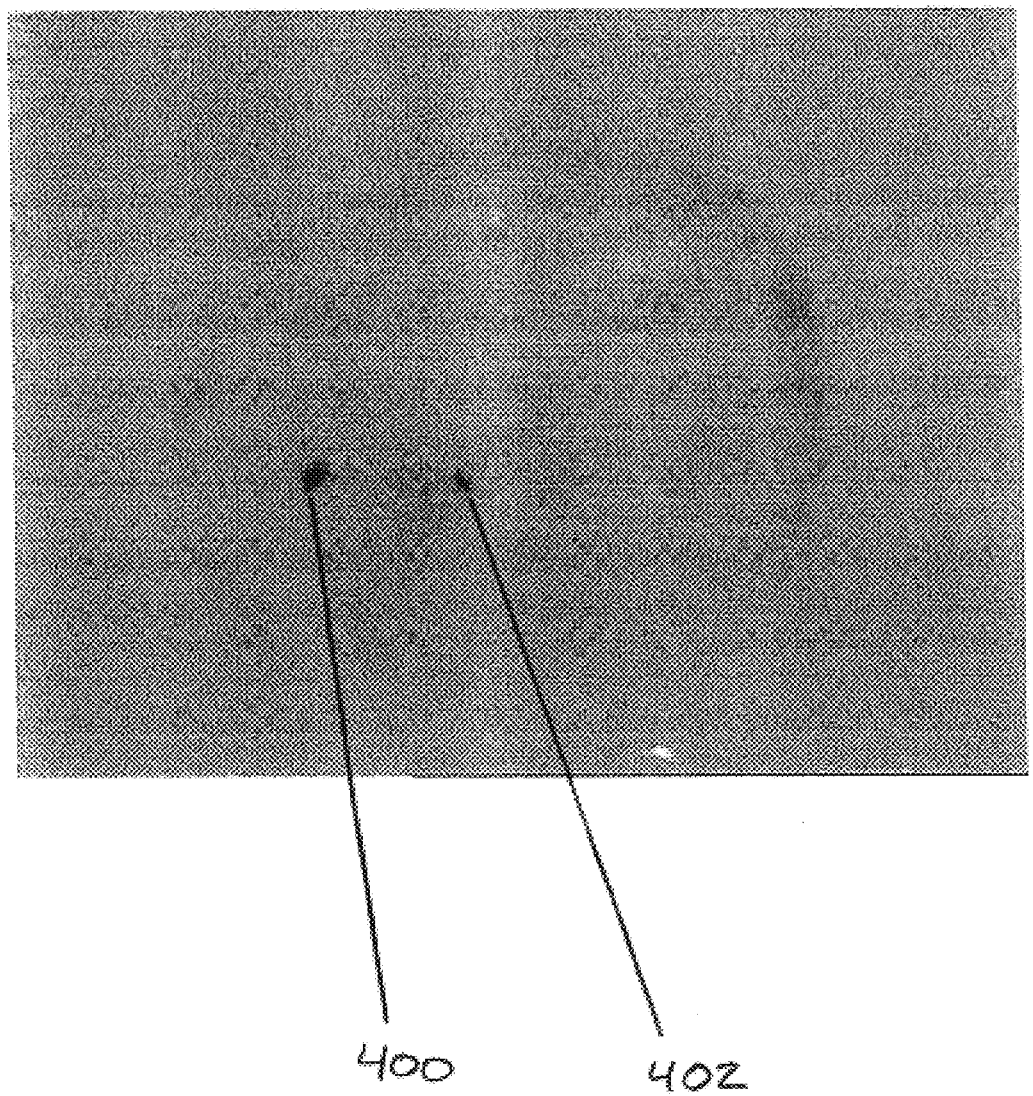
FIG. 4a is an image of a material particle created using the method and apparatus of the present invention.
Figure 4B:
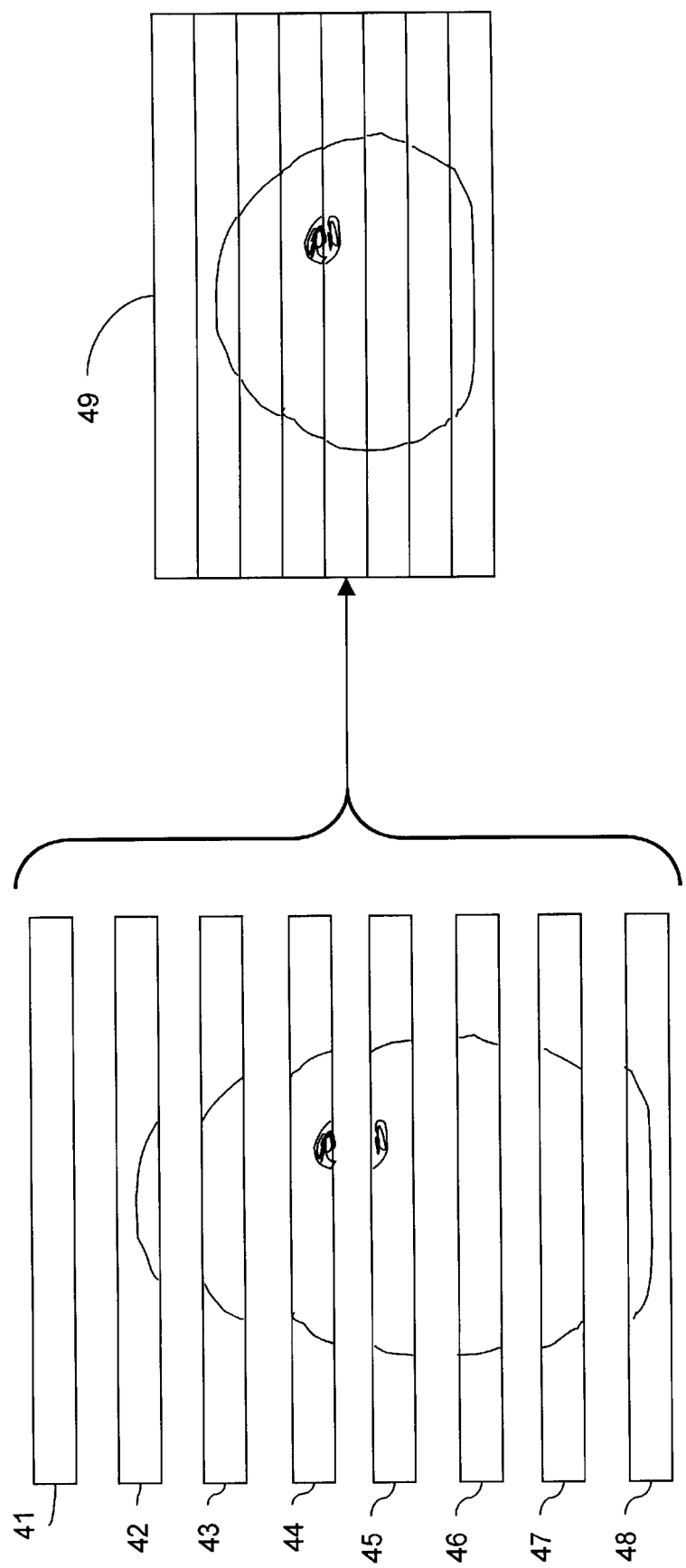
FIG. 4b is a schematic representation of the recording of one-dimensional lines and the assembling of the lines into a two dimensional image.
Figure 5:
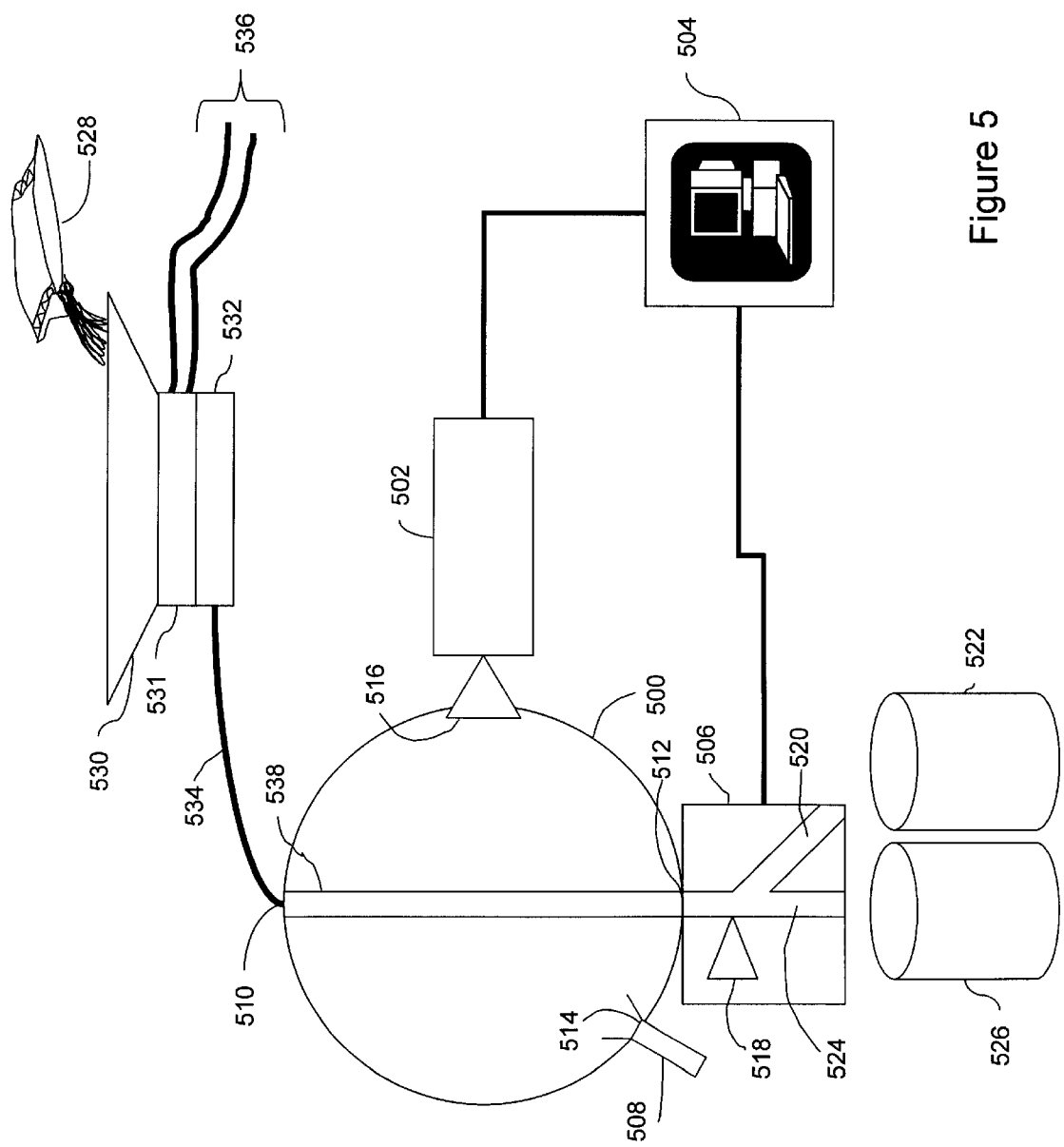
FIG. 5 is a schematic diagram of the method and apparatus of the present invention.

Referring to FIG. 5, the present invention comprises a light container 500, a camera 502, a digital processor 504, and a reject mechanism 506. The light container 500 comprises a light beam 508 and various openings or windows including a particle entry opening 510, a particle exit opening 512, a light beam opening or window 514, and at least one camera opening 516. In the preferred embodiment of the present invention, light container 500 is an integrating sphere that reflects light beam 508 in its interior to produce a diffuse, uniform, and spatially integrated field of light within light container 500. Also, preferably, light beam 508 does not transmit light directly to the location at which particles pass in front of camera 502 to avoid distorting the images with glares off of the particles.

Camera 502 views the center of the interior of light container 500 through camera opening 516. Camera 502 can be any device capable of electronically recording the illuminated image of a particle, including a standard video camera. However, in the preferred embodiment, camera 502 is a line scan camera that records the image of a particle in a sequence of one-dimensional arrays as the particle passes through the viewing field of the camera.

Figure 6:
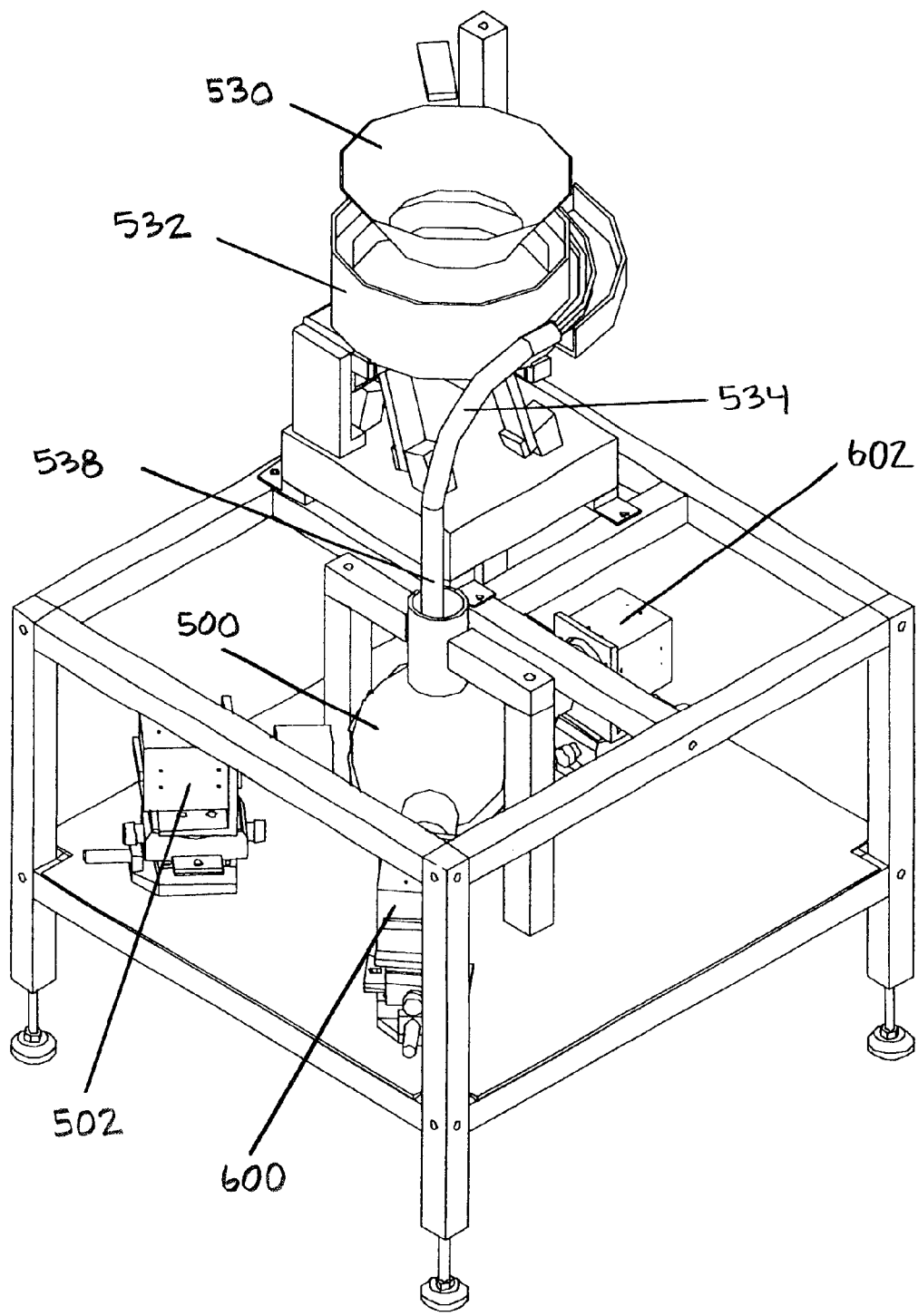
FIG. 6 is an isometric drawing illustrating an assembly of the present invention.

Although FIG. 5 shows only one camera for simplicity, the preferred embodiment of the present invention uses multiple cameras that capture multiple images of a particle, as shown in FIG. 6. Having multiple cameras reduces the possibility of a defect hiding behind a particle and improves the accuracy of the present invention. Cameras additional to camera 502 would be spaced around light container 500 but would never be on exact opposite sides of light container 500 (to avoid one camera capturing the opposing camera in an image, which might be mistaken for a defect). Also, the addition of one or more cameras would require additional openings or windows in light container 500. Preferably, the present invention uses an odd number of cameras spaced equally around light container 500.

Digital processor 504 receives the image information captured by camera 502 and analyzes the image for defects. In the preferred embodiment of the present invention, digital processor 504 is a computer that receives and stores in a memory buffer the one dimensional arrays recorded by camera 502. Camera 502 is preferably a line scan camera. Optionally, digital processor 504 and camera 502 are an integrated device. Digital processor 504 assembles the one-dimensional line scans into a two-dimensional image and identifies dark spots indicative of a defect. In addition, digital processor 504 is provided with the speed (e.g., inches per second) at which particles are moving through light container 500 so that when digital processor 504 detects a defect, it sends a signal to reject mechanism 506 at the exact time that the defective particle reaches reject mechanism 506. In the preferred embodiment in which the particles fall through light container 500, the particle speed is easily determined, since the particles' motion is essentially determined solely by their acceleration due to gravity. Alternatively, sensors could be connected to digital processor 504 to monitor particle speed for particles that are conveyed through light container 500 by means other than gravity. In addition, the present invention could use at least two sensors that measure rate (e.g., number of pellets per minute) to ensure that the rate of particles entering light container 500 equals the rate of particles exiting, with the purpose of monitoring for clogs or jams.

Reject mechanism 506 removes a defective particle in response to a signal from digital processor 504. Reject mechanism 506 must be precise enough to reject only the specific rejected particle in the stream of particles. Preferably, reject mechanism 506 incorporates a pneumatic jet 518 that delivers a short blast of air that redirects a particle into a reject channel 520. Reject channel 520 leads to a rejected particle bin 522 that collects the defective particles. The non-reject channel 524 conveys non-defective particles to a non-refect particle bin 526, or in the case of an in-line inspection process, to the next step in the manufacturing line.

The preferred embodiment of the present invention also includes several material handling components that help deliver a stream of evenly spaced particles through light container 500 and in front of camera 502. The goal of this material handling is to line up the particles so as to present one particle at a time to camera 502, preferably at intervals (i.e., with a separation between one particle and the next). In addition, to facilitate in-line inspection processes, the material handling components should preferably (but not necessarily) sort particles of different types, e.g., sizes, before the particles are inspected in light container 500. As shown in FIG. 5, bulk raw material 528 of different types is added to a hopper 530. Hopper 530 is any receptacle that temporarily holds bulk raw material 528 and funnels or channels it for delivery to a next material handling component.

That next component is a sorting mechanism 531, which separates bulk raw material 528 into portions of particles with a same characteristic, e.g., sorting mechanism 531 selects particles of roughly the same size, or particles that are unbroken. In the preferred embodiment, sorting mechanism 531 separates bulk raw material 528 into homogeneous portions at a rate equal to or above the rate of the manufacturing line. An example of an acceptable sorting mechanism is a sifting sorter (e.g., a screen sorter) or a size sorter.

Once sorting mechanism 531 has separated bulk raw material 528, each homogeneous portion is delivered to separate feeders connected to material inspection apparatus. In FIG. 5, sorting mechanism 531 delivers particles to a feeder 532 attached to the apparatus shown in the figure, while other conduits 536 deliver particles of other sizes to other feeders connected to other inspection apparatus (not shown) or simply discard the other-size particles into waste bins for recycling.

Feeder 532 separates each particle and lines up the particles for one-by-one delivery through conduit 534 to light container 500. Feeder 532 accomplishes this task using any conventional means, e.g., a vibrating bowl or a linear feeder.

Another preferred material handling component is a clear conduit 538 that connects particle entry opening 510 to particle exit opening 512. Clear conduit 538 ensures that each particle follows a defined path that always passes through the field of view of camera 502. At a minimum, the section of clear conduit 538 in the field of view of camera 502 must be transparent so that the particle can be fully illuminated and camera 502 can record an image.

Also, for improved material handling, one or more particle counters could be added to the preferred embodiment for purposes of quality control. For example, a first particle counter could be located at the discharge of feeder 532 and a second particle counter could be located at the inlet of reject mechanism 506. In this manner, the present invention could determine if particles have jammed and are no longer flowing.

FIG. 6 is an isometric drawing illustrating how the present invention might be assembled. In this configuration, multiple cameras 502, 600, and 602 view the interior of light container 500. The remaining components labeled with element numbers correspond to the components shown in FIG. 5.

Method of the Present Invention

Once the material handling components have sorted and lined up the particles, the present invention inspects every particle for defects, identifies defective particles, and separates the particles into approved and rejected portions. Each particle passes through light container 500, so that every portion (even the edges) of each particle is fully illuminated when recorded by camera 502.

FIG. 5 illustrates a configuration in which particles fall by gravity through clear conduit 538 and pass in front of camera 502. Although gravity is the preferred means of conveyance because of its simplicity, any other means of conveyance could be used as long as it does not obstruct the illumination of the particle or the view of camera 502. In addition, in the preferred embodiment, the particles drop a short distance, e.g., three inches, to minimize the velocity at which they pass in front of camera 502.

The operation of camera 502 favors minimal particle velocity to reduce the rate at which it must record line scans and to improve the accuracy and resolution of the one-dimensional arrays and two-dimensional images. The number of times a one-dimensional array is recorded within a specific time interval is referred to as the line rate. Camera 502 sends each recorded array to digital processor 504, which adds each array to the two-dimensional image stored in memory. At a specified time, referred to as the frame time, digital processor 504 retrieves from memory the two-dimensional image, or frame, to analyze the image for defects. The longer the frame time, the more one-dimensional arrays are stored in memory and included in the two dimensional image.

The frame time is set according to the specific configuration of an apparatus, depending on such factors as the time it takes a particle to travel from the field of view of camera 502 to reject mechanism 506 or simply the speed of a particle through light container 500. To reject particles, digital processor 504 marks the frame in which the defect was identified, waits the appropriate number of frames required for the particle to reach reject mechanism 506, and signals reject mechanism 506 to remove the defective particle. Thus, if the frame time is too long, a particle will fall past reject mechanism 506 prior to the completion of the frame in which the defect would be detected.

Figure 7:
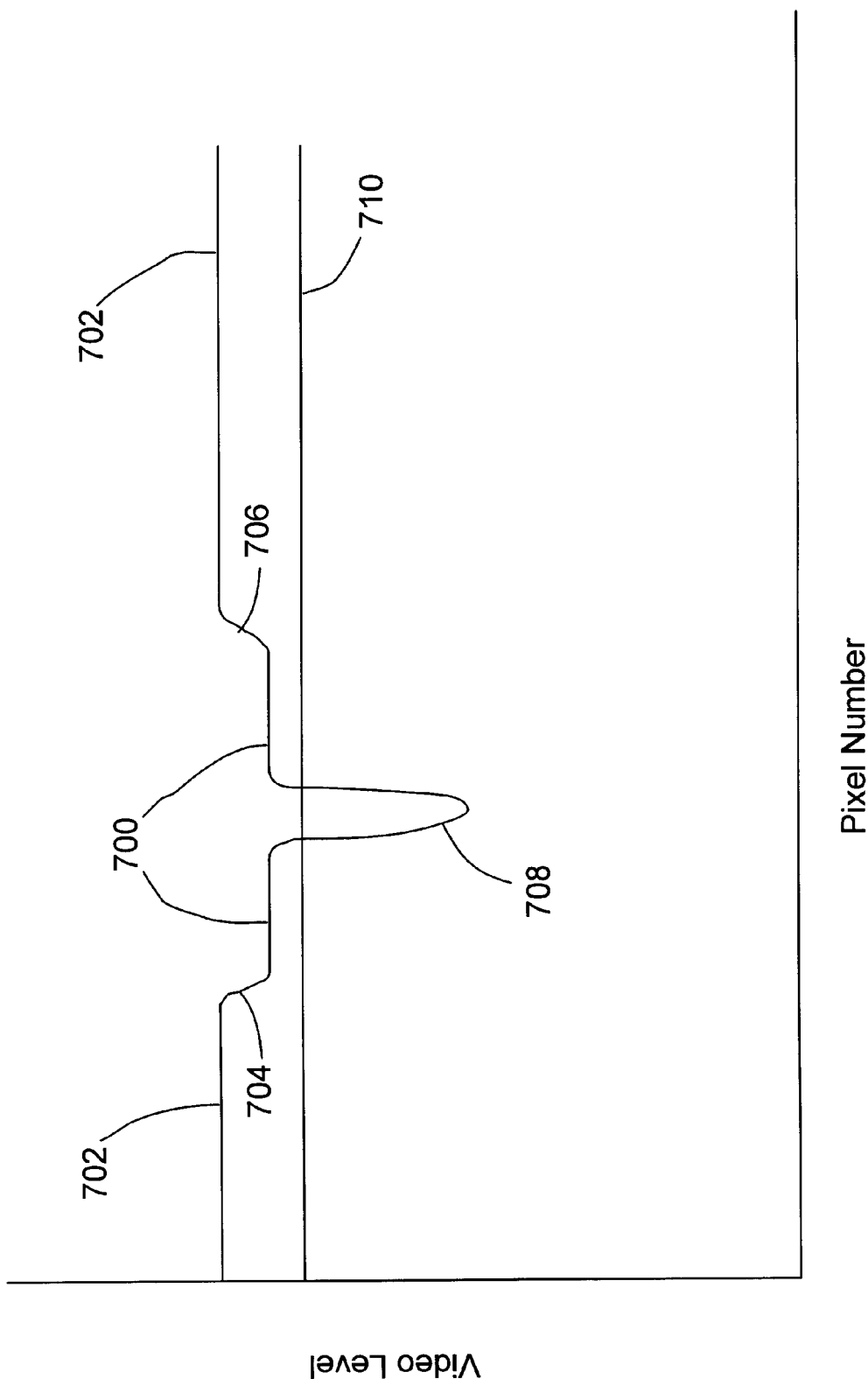
FIG. 7 is a graph of video level as a function of pixel number, illustrating the video response of a camera and digital processor of the present invention.

The method by which digital processor 504 identifies defects preferably involves a calibration step using camera 502. This calibration sets a threshold level based on the light properties of the material being inspected and the light properties of potential defects. To start, a sample of particles is scanned to determine the video level at which light passes through a non-defective particle, based on an average video gray level of the sample of particles. FIG. 7 shows this non-defective particle video gray level 700 on a display of video level as a function of pixel number. On this display, the pixel numbers correspond to consecutive pixels in a line scan, while the video level corresponds to the lightness or darkness of the line scan image. For the video level, the lower the value is, the darker the image appears. Each line scan records a fixed amount of pixels, e.g., 512 pixels, each of a particular video level. The video level above non-defective particle video level 700 is the light container video level 702, representing points at which camera 502 is viewing light directly from the interior surfaces of light container 500 without going through a particle. The transition points 704 and 706 between light container video level 702 and non-defective particle video level 700 represent the beginning and ending edges of the particle, respectively.

Finally, defect video level 708 represents points at which a defect is detected in the particle.

The goal in calibrating digital processor 504 to detect defects is to distinguish between the video level of a particle and the lower video level of a defect in the particle. Thus, in FIG. 7, a threshold level 710 is established, which represents a point at which the video level is too low to be a non-defective particle video level and is low enough to be a defect video level. If threshold level 710 is set too low, minor defects that do not produce the lowest video level may pass undetected. Thus, the setting of the threshold is largely a balancing between missing minor defects and triggering false positives because threshold level 710 is too close to the non-defective particle video level 700. In addition, it should be noted that threshold level 710 must be set for each type of material.

Based on the calibration, digital processor 504 identifies the reject and signals the reject mechanism 506 every time a video level drops below threshold level 710. In response, reject mechanism 506 removes the defective particle from the raw material.

As an alternative to the calibration technique described above, the present invention could use other image processing methods to detect defects. For example, blob analysis software, available from Matrox Electronics System Ltd., Quebec, Canada, would be a suitable image processing technique. In addition, pattern matching analysis would be suitable to detect defects in images.

By using the threshold level, the present invention looks only for the presence of defects and does not track the beginning or ending edges of a particle. Thus, the present invention offers the advantage of being able to accommodate particles of any shape. Typically, plastic pellets are in regular or irregular cylindrical and spherical forms, whereas food products can have any shape. Thus, the present invention is especially advantageous for inspecting food particles of irregular shapes, such as rice. In any case, the present invention will operate to reject a particle with a defect regardless of the particle's shape.

In addition to shapes, the present invention can be adapted to inspect other particle sizes. In a typical application, for inspecting plastic pellets ranging from 2 to 5 millimeters in diameter, the distance from entry in light container 500 to the field of view of the camera is approximately three inches. If larger particles need to be inspected, the components of the present invention can be simply increased by an appropriate scale (e.g., using a larger light container).

The present invention may also be customized to be more sensitive to the suspected particle defects. For example, if the material supplier wishes to identify gels in plastic pellets instead of only contaminants, an ultraviolet light beam would be used and defects would be detected from the fluorescence of the gels. Certain defective material absorbs ultraviolet light and emits a longer wavelength of visible light in a different way than the non-defective material. The resulting image shows a defective portion brighter than the rest of the pellet. For example, under ultraviolet light, non-defective portions of the pellet may emit a blue glow, while the defective portions emit a stronger blue glow or, perhaps, a bright orange glow. In any case, the differentiation in glow caused by the fluorescence enables the present invention to identify these particular types of plastic pellet defects (e.g., gels). U.S. Pat. No. 5,383,776, which is incorporated herein by reference, discloses an example of this technique of using fluorescence to detect polymer defects.

Figure 8:
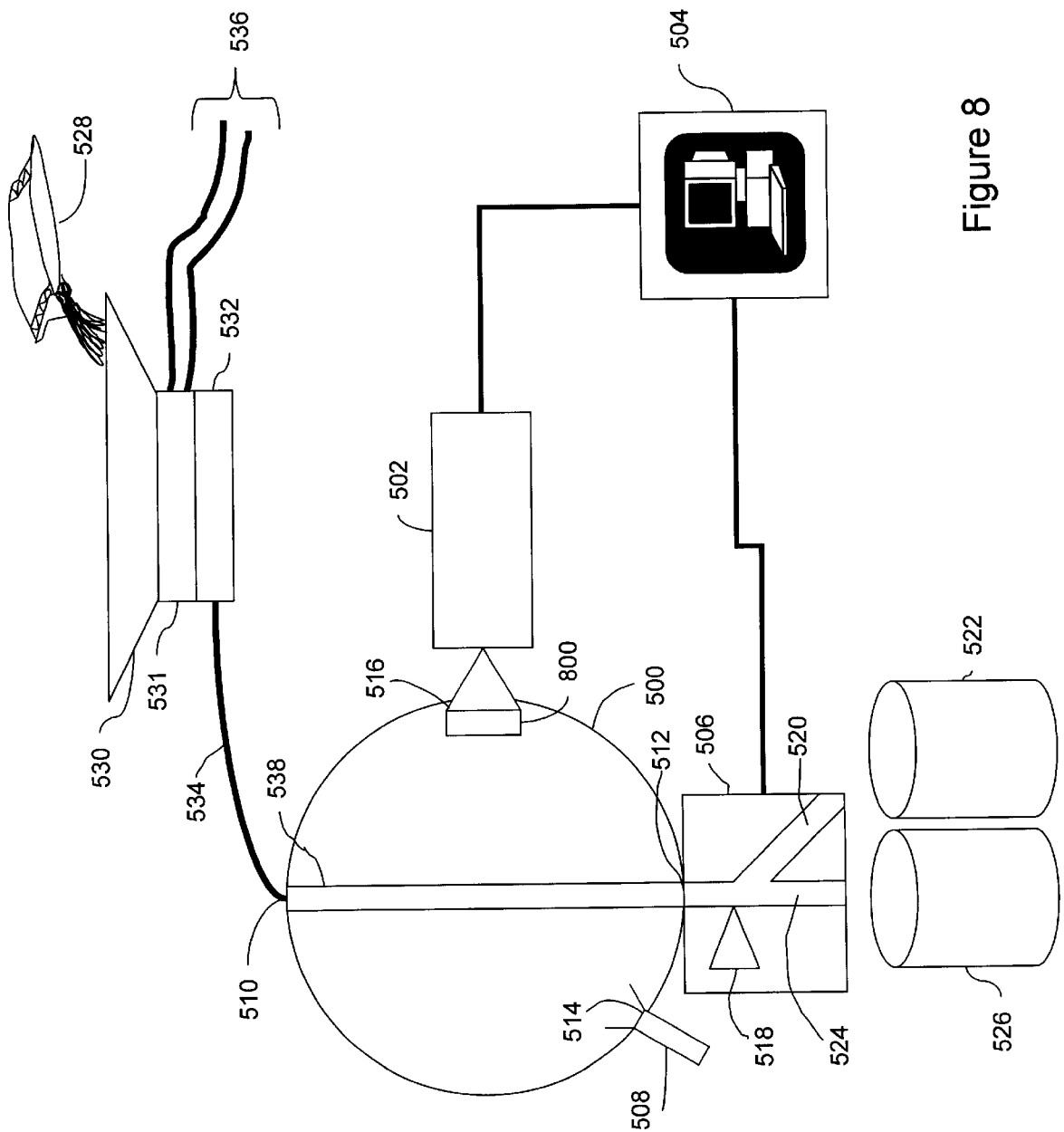
FIG. 8 is a schematic diagram of the method and apparatus of the present invention using an ultraviolet light beam to detect gels.

To detect defects with ultraviolet light, a preferred embodiment of the present invention, as shown in FIG. 8, uses a camera filter 800 to attenuate the light emitted from non-defective portions and to accentuate the light emitted from defective portions. For example, in a plastic that emits a blue glow for non-defective portions and an orange glow for defects, the present invention would use an orange filter that passes only a narrow band of light in the orange spectrum. The resulting image would show a defect as a bright speck on a dark background.

Figure 9:
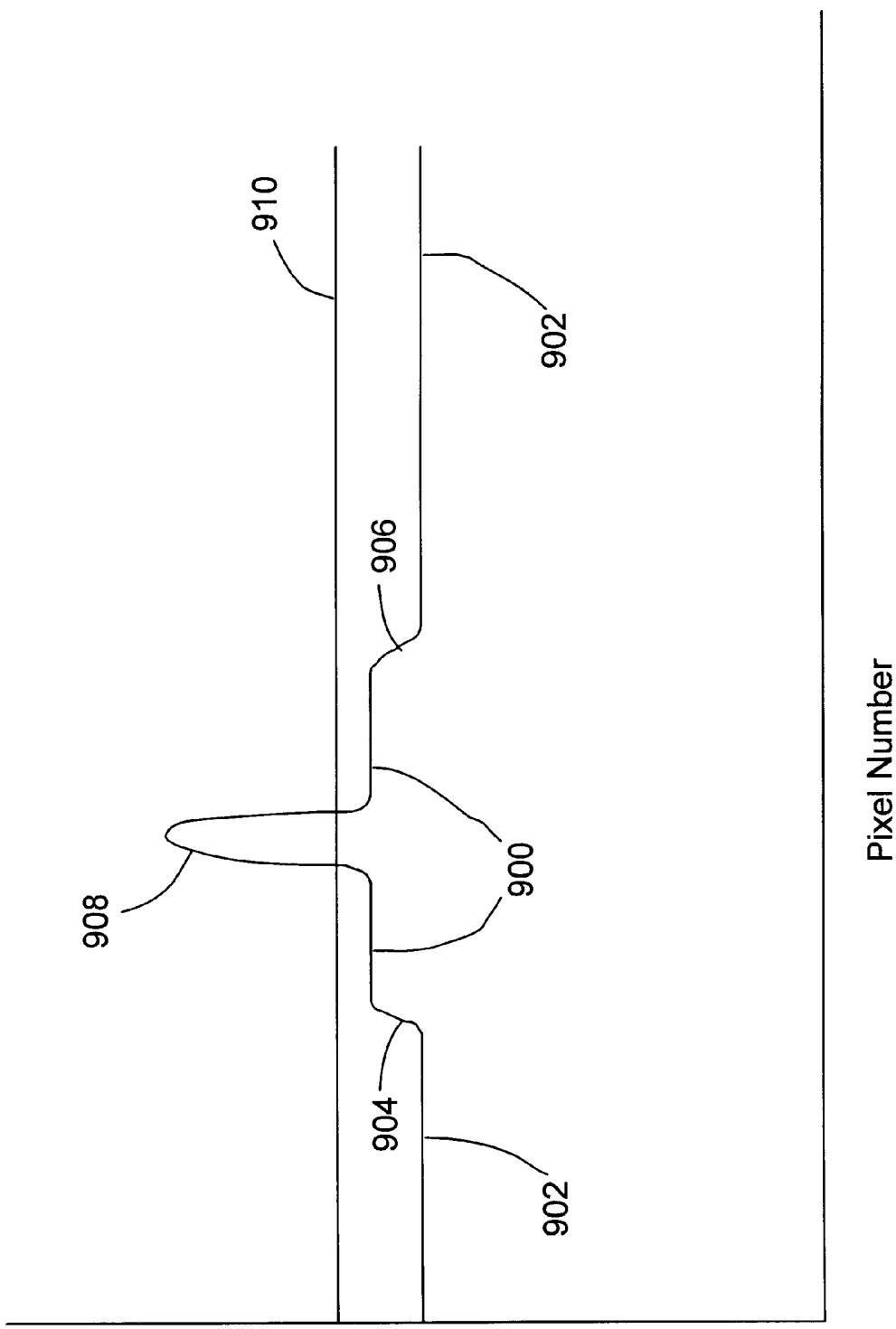
FIG. 9 is a graph of video level as a function of pixel number, illustrating the video response of a camera and digital processor for the ultraviolet light embodiment of the present invention shown in FIG. 8.

Using ultraviolet light also requires calibrating the video levels of camera 502 differently than described above. Because the ultraviolet light makes defects brighter than the remainder of a pellet, the particle and threshold levels shown in FIG. 7 are essentially inverted. FIG. 9 shows the non-defective particle video level 900 on a display of video level as a function of pixel number. As with FIG. 7, the lower the value of the video level is, the darker the image appears. The video level below non-defective particle video level 900 is the light container video level 902, representing points at which camera 502 is viewing light directly from light container 500 without going through a particle. The transition points 904 and 906 between light container video level 902 and non-defective particle video level 900 represent the beginning and ending edges of the particle, respectively. Finally, defect video level 908 represents points at which a defect is detected in the particle.

The goal in calibrating digital processor 504 to detect defects with ultraviolet light is to distinguish between the video level of a particle and the higher video level of a defect in the particle. Thus, in FIG. 9, a threshold level 910 is established, which represents a point at which the video level is too high to be a non-defective particle video level and is high enough to be a defect video level.

Thus the present invention could use any source of electromagnetic radiation, including white light, blue light, red light, green light, yellow light, visible light, infrared light, or ultraviolet light, selected for the specific inspection application. For convenience, the term "light" in the claims shall refer to all the types of electromagnetic radiation listed in this paragraph, unless the term is modified by an adjective.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art of light of the above disclosure. The scope of the invention is to be defined only by the claims appended hereto, and by their equivalents.

What is claimed is:

1. A material inspection apparatus comprising:
   (a) a light container having an entry opening and an exit opening;
   (b) at least one camera with an inside view of the light container,
   wherein the at least one camera is adapted to capture an image of a particle traveling from the entry opening to the exit opening as the particle is illuminated inside the light container;
   (c) a reject mechanism in fluid communication with the exit opening; and
   (d) a digital processor in signal communication with the at least one camera and with the reject mechanism.

2. The material inspection apparatus of claim 1, wherein the digital processor is a computer with means for receiving data from the at least one camera, assembling the data into images, analyzing the images for defects, and sending a signal to the reject mechanism.

3. The material inspection apparatus of claim 1, wherein the at least one camera and the digital processor are an integrated device.

4. The material inspection apparatus of claim 1, wherein the reject mechanism removes a defective particle in response to a signal from the digital processor.

5. The material inspection apparatus of claim 1, wherein the reject mechanism comprises:
   (i) a signal receiver;
   (ii) a non-reject channel in fluid communication with the exit opening;
   (iii) a reject channel in fluid communication with the non-reject channel; and
   (iv) a pneumatic injector in fluid communication with the non-reject channel, the pneumatic injector capable of redirecting a defective particle from the non-reject channel to the reject channel.

6. The material inspection apparatus of claim 1, wherein the at least one camera, the reject mechanism, and the digital processor work automatically as a part of a manufacturing process.

7. A material inspection apparatus comprising:
   (a) a light container having an entry opening and an exit opening;
   (b) at least one camera with an inside view of the light container,
   wherein the at least one camera is adapted to capture an image of a particle traveling from the entry opening to the exit opening as the particle is illuminated inside the light container;
   (c) a feeder that receives particles in bulk;
   (d) a sorting mechanism in fluid communication with the feeder and with the entry opening;
   (e) a clear conduit connecting the entry opening to the exit opening; and
   (f) at least one particle counter that counts particles traveling through the light container.

8. A method for inspecting particles comprising the steps of:
   (a) sorting the particles and arranging the particles into a line of particles;
   (b) conveying the line of particles one-by-one through a light container;
   (c) recording images of the particles as the particles are illuminated inside the light container; and
   (d) identifying defects in the images.

9. The method of claim 8, wherein the light container is an integrating sphere with an input beam, and wherein the input beam transmits light into the integrating sphere but away from the particles.

10. The method of claim 8, wherein the light container is an integrating sphere.

11. The method of claim 8, wherein the step of conveying comprises dropping the particles through a clear conduit running through the light container.

12. The method of claim 8, wherein the step of recording images of the particles comprises the steps of:
   (i) scanning one-dimensional arrays of the particles as the particles pass in front of a line scan camera;
   (ii) sending the one dimensional arrays to a memory buffer in a digital processor; and
   (iii) assembling the one-dimensional arrays into a two dimensional image at a specified frame time.

13. The method of claim 8, wherein the step of identifying defects comprises the steps of:
   (i) scanning a sample of particles to determine a non-defect video level at which light passes through a non-defective particle;
   (ii) determining a defect video level that indicates a defective particle;
   (iii) establishing a threshold level between the non-defect video level and the defect video level; and
   (iv) identifying the defects as instances when a video level of the images falls below the threshold level.

14. The method of claim 8, further comprising the steps of:
   (e) associating the defects in the images with defective particles in the line of particles; and
   (f) removing the defective particles from the line of particles.

15. The method of claim 14, wherein the step of removing the defective particles comprises injecting air to redirect the defective particles to a destination separate from a destination of the line of particles.

16. A method for inspecting particles comprising the steps of:
   (a) passing the particles through a light container;
   (b) scanning the particles; and
   (c) identifying defective particles,
   wherein the particles pass through the light container one-by-one in a line.

17. The method of claim 16, wherein the light container is an integrating sphere.

18. The method of claim 16, wherein the particles pass through the light container in a clear conduit.

19. A method for inspecting particles comprising the steps of:
   (a) passing the particles through a light container;
   (b) scanning the particles; and
   (c) identifying defective particles,
   wherein the step of scanning the particles comprises recording one-dimensional arrays of the particles and assembling the one-dimensional arrays into images of the particles.

20. The method of claim 19,
   wherein the step of identifying defective particles comprises recognizing dark areas in the images of the particles.

21. A method for inspecting particles comprising the steps of:
   (a) passing the particles one-by-one through a light container;
   (b) scanning the particles; and
   (c) identifying defective particles,
   wherein the particles are transparent or translucent.

22. A method for inspecting particles comprising the steps of:
   (a) passing the particle one-by-one through a light container;
   (b) scanning the particles; and
   (c) identifying defective particles,
   wherein the particles are opaque.

23. A system for inspecting particles comprising:
   (a) an integrating sphere that produces spatially integrated light;
   (b) means for sorting the particles into a stream of particles and directing the stream of particles through the integrating sphere;

(c) means for electronically recording images of the particles as they pass through the integrating sphere;

(d) means for identifying flawed particles by detecting dark spots in the images of the particles; and (e) means for rejecting flawed particles.

24. The system of claim 23, wherein the means for sorting the particles comprises a sifting sorter.

25. The system of claim 23, wherein the means for electronically recording images of the particles comprises a line scan camera.

26. The system of claim 25, comprising a digital processor that stores one-dimensional arrays recorded by the line scan camera, and assembles the one-dimensional arrays into two-dimensional images.

27. The system of claim 23, wherein the means for rejecting the flawed particles comprises a pneumatic injector in communication with the means for identifying the flawed particles.

* * * * *